US012589239B2

(12) United States Patent
Gandhi et al.

(10) Patent No.: US 12,589,239 B2
(45) Date of Patent: Mar. 31, 2026

(54) USE OF OPTICAL FIBER SENSOR AS A DIAGNOSTIC TOOL IN CATHETER-BASED MEDICAL DEVICES

(71) Applicant: ABIOMED, Inc., Danvers, MA (US)

(72) Inventors: Rahul Suresh Gandhi, Danvers, MA (US); Tao Zhang, Danvers, MA (US)

(73) Assignee: Abiomed, Inc., Danvers, MA (US)

( * ) Notice: Subject to any disclaimer, the term of this patent is extended or adjusted under 35 U.S.C. 154(b) by 332 days.

(21) Appl. No.: 18/102,947

(22) Filed: Jan. 30, 2023

(65) Prior Publication Data

US 2023/0173251 A1     Jun. 8, 2023

Related U.S. Application Data

(62) Division of application No. 16/577,011, filed on Sep. 20, 2019, now Pat. No. 11,628,293.

(Continued)

(51) Int. Cl.
*A61M 60/538*        (2021.01)
*A61M 60/13*          (2021.01)
(Continued)

(52) U.S. Cl.
CPC .......... *A61M 60/538* (2021.01); *A61M 60/13* (2021.01); *A61M 60/216* (2021.01); *A61M 60/422* (2021.01); *A61M 60/531* (2021.01); *A61M 60/818* (2021.01); *A61M 60/90* (2021.01); *F04B 17/03* (2013.01); *F04B 51/00* (2013.01); *G01R 31/343* (2013.01);
(Continued)

(58) Field of Classification Search
None
See application file for complete search history.

(56) References Cited

U.S. PATENT DOCUMENTS 6,398,506 B1     6/2002   Maekawa et al.
9,669,142 B2     6/2017   Spanier et al.
(Continued)

FOREIGN PATENT DOCUMENTS

CA         2428846 A1     12/2003
CN       104162191 A      11/2014
(Continued)

OTHER PUBLICATIONS

Office Action from corresponding Indian Patent Application No. 202117015650 dated Apr. 22, 2024 (2 pp.).
(Continued)

*Primary Examiner* — Unsu Jung
*Assistant Examiner* — Sefra D. Manos
(74) *Attorney, Agent, or Firm* — Botos Churchill IP Law LLP

(57)                ABSTRACT

A blood pump system including an optical sensor configured to detect an optical signal during pumping operation of the blood pump, and an optical fiber configured to transmit the optical signal from the optical fiber sensor to an evaluation device communicatively coupled to the optical fiber sensor. The evaluation device is configured to receive as inputs the transmitted optical signal and a signal indicative of the motor current and determine a mechanical failure event associated with the blood pump based on the motor current and the optical signal.

4 Claims, 8 Drawing Sheets

Related U.S. Application Data

(60) Provisional application No. 62/734,702, filed on Sep. 21, 2018.

(51) Int. Cl.

| | |
|---|---|
| *A61M 60/216* | (2021.01) |
| *A61M 60/411* | (2021.01) |
| *A61M 60/422* | (2021.01) |
| *A61M 60/531* | (2021.01) |
| *A61M 60/818* | (2021.01) |
| *A61M 60/90* | (2021.01) |
| *F04B 17/03* | (2006.01) |
| *F04B 51/00* | (2006.01) |
| *G01R 31/34* | (2020.01) |

(52) U.S. Cl.
CPC ... *A61M 60/411* (2021.01); *A61M 2205/3306* (2013.01); *A61M 2205/3331* (2013.01); *A61M 2205/3365* (2013.01)

(56) References Cited

U.S. PATENT DOCUMENTS

| | | | | |
|---|---|---|---|---|
| 9,669,144 | B2 | 6/2017 | Spanier et al. | |
| 9,726,476 | B2 | 8/2017 | Ramamurthy et al. | |
| 10,561,773 | B2 * | 2/2020 | Ferrari | A61M 60/139 |
| 2003/0095322 | A1 | 5/2003 | Gehlot | |
| 2005/0008496 | A1 | 1/2005 | Tsubouchi et al. | |
| 2015/0087890 | A1 | 3/2015 | Spanier et al. | |
| 2015/0141842 | A1 * | 5/2015 | Spanier | A61M 60/237 |
| | | | | 600/478 |
| 2015/0290372 | A1 | 10/2015 | Muller et al. | |

| | | | | |
|---|---|---|---|---|
| 2016/0050470 | A1 | 2/2016 | Swinkels et al. | |
| 2016/0161296 | A1 | 6/2016 | Handerek | |
| 2017/0049945 | A1 * | 2/2017 | Halvorsen | A61M 60/88 |
| 2017/0173275 | A1 | 6/2017 | Anderson et al. | |
| 2018/0078159 | A1 | 3/2018 | Edelman et al. | |

FOREIGN PATENT DOCUMENTS

| | | | |
|---|---|---|---|
| EP | 2796156 A1 | 10/2014 | |
| JP | 2005028137 A | 2/2005 | |
| JP | 2005080982 A | 3/2005 | |
| JP | 2015515348 A | 5/2015 | |
| KR | 20060000539 A | 1/2006 | |
| WO | 2012108475 A1 | 8/2012 | |
| WO | WO-2018031741 A1 * | 2/2018 | A61M 1/10 |

OTHER PUBLICATIONS

Office Action from corresponding Korean Patent Application No. 10-2021-7007209 dated Jun. 14, 2024 (11 pp.).

Office Action from corresponding Japanese Patent Application No. 2021-515559 dated Jul. 31, 2023 (6 pp.).

Office Action issued in corresponding Chinese Patent Application No. 2019800610431 dated Aug. 18, 2023 (12 pp.).

Xing, Zhu, Technological Revolution and the Development of Artificial Kidney, Journal of Medical Information, Mar. 31, 2009, pp. 419-422.

International Search Report and Written Opinion for Application No. PCT/US2019/052063 dated Dec. 20, 2019.

Office Action issued in Indian Patent Application No. 202117015650 dated Nov. 30, 2022 (4 pp.).

Office Action issued in corresponding Japanese Patent Application No. 2024-059358, mailed Feb. 13, 2025, 4 pages.

* cited by examiner

USE OF OPTICAL FIBER SENSOR AS A DIAGNOSTIC TOOL IN CATHETER-BASED MEDICAL DEVICES

CROSS-REFERENCE TO RELATED APPLICATIONS

This application is a divisional of U.S. application Ser. No. 16/577,011, filed on Sep. 20, 2019, now allowed, which application claims the benefit of priority to U.S. Provisional Application No. 62/734,702, filed Sep. 21, 2018, and entitled "USE OF OPTICAL FIBER SENSOR AS A DIAGNOSTIC TOOL IN CATHETER-BASED MEDICAL DEVICES". The entire contents of the foregoing applications are incorporated herein by reference.

BACKGROUND OF THE INVENTION

Catheter-based medical devices can be monitored to ensure that the device is operating normally. For example, early and reliable detection of a bearing failure in a blood pump can help prevent any sudden stop of the pump and the associated adverse effects to the patients. Some blood pumps use the motor current as a sensing signal to monitor pump performance. But motor current does not always capture the early signs of bearing failure and can be affected by other factors.

Blood pumps can be integrated with a fiber optic pressure sensor to monitor the placement of the pump in the vasculature of a patient. In addition to monitoring the pressure signal, the fiber optic sensor can be used to monitoring stress/strain, temperature, and vibration. For example, as described in U.S. Pat. No. 9,669,144, the fiber optic sensor can be used to monitor kinks in the catheter. But optical fiber sensors have not been adopted to detect ongoing operational characteristics of catheter-based medical devices.

BRIEF SUMMARY OF THE INVENTION

The systems, methods, and devices described herein provide for using an optical fiber sensor as a diagnostic tool to evaluate the performance and status, and ultimately detect potential failure, of a catheter-based medical device. Adaptations of the systems may include an optical sensor and an optical fiber connecting the sensor to a monitor or other signal processing device configured to receive input signals from the sensor and determine characteristics of the medical device. In some implementations, the tool is used to detect a mechanical failure of a blood pump. Embodiments are disclosed for a blood pump system including an optical sensor configured to detect an optical signal during pumping operation of the blood pump, and an optical fiber configured to transmit the optical signal from the optical fiber sensor to an evaluation device communicatively coupled to the optical fiber sensor. The sensor is positioned near the pump so as to detect perturbations in the blood caused by pumping action of the pump and which changes or deforms the optical sensor head. The sensor head deforms based on the pressure of the blood pressing against the sensor head. When the sensor head is deformed, light bounces around into the sensor fiber and is picked up by the evaluation device. This reflected light is compared to a reference or baseline signal and a pressure signal is extracted from the comparison. Using the reflected light, the sensor can also detect perturbations in the blood caused by vibrations in the pump housing, the rotor, the motor, or the cannula that is included in the pump system. In some adaptations, the sensor is attached to the pump housing or placed adjacent to the pump housing, or placed near the pump motor (in the case of an implanted motor). The evaluation device may be configured to receive as inputs the transmitted optical signal and a signal indicative of pump motor current and determine a mechanical failure event associated with the pump based on the motor current and the optical signal.

The tool may be used in combination with one or more other parameters, for example motor current readings and other sensor readings such as placement signal and flowrate, for enhanced detection. In a first implementation, the tool is implemented in a blood pump system including a catheter having proximal and distal ends, a blood pump having a motor coupled to the catheter, an optical sensor configured to detect an optical signal during pumping operation of the blood pump, and an optical fiber extending through the catheter and configured to transmit the optical signal from the optical sensor to an evaluation device communicatively coupled to the optical sensor. The optical sensor is positioned at or near the pump so as to detect perturbations in the blood resulting from the pumping action of the pump. The evaluation device is configured to receive the input signal and determine whether a mechanical failure event associated with the blood pump has occurred. In certain implementation, that determination is made based on the input optical signal and a motor current of the blood pump motor. If the pump stops pumping or encounters resistance during operation, the optical signal (and the noise associated with it) will change because of the change in vibrations of the motor, the pump, or pump components or the cannula, and that change can be detected by the evaluation device. The evaluation device can be cannula, and that change can be detected by the evaluation device. The evaluation device can be current, calculate a signal to noise ratio (SNR) of the optical signal, receive a predetermined threshold for SNR, compare the calculated SNR to the predetermined threshold, and determine a mechanical failure event associated with the blood pump, pump components, cannula or pump motor.

Changes in the SNR may be indicative of problems with the pump. The SNR is correlated to the vibrations of the blood pump, or vibrations of components of the system, such as the cannula or the motor (as used herein, the vibrations of the pump refer generally to mechanical vibrations of the implanted device, including the pump, its components, or the cannula, or a motor, that occur when the device is operating in vivo). When the motor is stopped, the pump also stops and, accordingly, the motor current is zero and the vibrations are at a minimum. During this state, the SNR is relatively large because the noise level of the optical signal is low due to low mechanical vibration of the pump. In normal conditions, when the motor is running, the motor current is greater than zero and the vibration of the pump increases. During this state, the SNR is relatively low because the noise level of the optical signal is large. A mechanical failure event may occur that causes the pump to jam, slow or stop altogether. In such a state, the failure may be detected when, over a time period, the motor current is greater than zero (indicating that the motor is driving current) but the SNR increases, for example the calculated SNR increases during the time period until exceeds a predetermined threshold. Having a motor current greater than zero indicates that the motor is operating as if the pump were performing normally, yet an increase in SNR indicates that the pump is experiencing more vibrations, which could indicate that the pump is failing even as it continues to pump (e.g., the bearings could be wearing down).

The evaluation device may be configured to generate and output, in response to determining the mechanical failure event, an indicator associated with the mechanical failure event.

In some implementations, the evaluation device is configured to determine the threshold based on a baseline SNR. The threshold may be the SNR (or an average) during normal pump steady state operation. In some implementations, the determined threshold is double a magnitude of the baseline SNR, or at least 3× or 10× or greater.

In certain implementations, the evaluation device is configured to determine a pressure signal based on the transmitted optical signal and use that signal to assess pump performance. For example, the evaluation device may be configured to determine the mechanical failure event based on the calculated SNR, the motor current, and the determined pressure signal.

The optical fiber is placed so as to receive a detectable signal that can readily be used for assessing device performance. In some implementations, the optical fiber sensor is attached to the pump housing, or to the catheter or cannula near the motor, but positioned so that it contacts blood flowing from the pump (or past the motor). According to certain implementations, the optical fiber sensor is located at the distal end of the catheter. In some implementations, the diagnostic tool includes a second optical fiber sensor that detects a second optical signal and a second optical fiber that transmits the second optical signal to the evaluation device. The second optical signal may be placed for example near the distal end of the pump (e.g., near pump inlet openings) to detect changes in the SNR of a pumping cadence associated with the distal end of the pump. Such signals may also be used to determine the mechanical failure event.

The time period for monitoring pump performance (and particularly the SNR and the motor current) can be adjusted by the user for short or long term monitoring. In some implementations, the time period is set between about 1 to about 5 minutes. According to certain implementations, the time period is between about 5 to about 10 minutes, or up to 6 hours, up to 24 hours or up to a week or longer.

The present disclosure also contemplates various methods, for example, it provides a method of determining a mechanical failure event of a blood pump during operation of the pump. The method comprises determining a motor current of a motor that drives the blood pump. The method also comprises detecting an optical signal at the blood pump during pump operation and transmitting the optical signal, using an optical fiber, from the optical sensor (e.g., placed near the pump housing or pump rotor) to an evaluation device. Further, the method comprises calculating, at the evaluation device, a signal to noise ratio (SNR) based on the transmitted optical signal. The method further comprises determining a mechanical failure event associated with the blood pump motor based on the calculated SNR and the determined motor current. Changes in the SNR may be indicative of problems (e.g., mechanical stresses that may lead to device failure) with the pump. In some configurations, a mechanical failure event is triggered when, over a time period, the motor current is greater than zero and an increase in the calculated SNR in the time period exceeds a predetermined threshold.

In some implementations, the method further comprises, in response to determining the mechanical failure event, generating and outputting a signal indicative of the mechanical failure event. For example, the signal indicative of the mechanical failure event may be transmitted to a processing system and displayed as an auditory alarm, a visual alarm, or both.

In certain implementations, the method further comprises determining the threshold based on a baseline SNR that occurs, for example, during normal operation of the pump. According to some implementations, the determined threshold is double a magnitude of the baseline SNR.

In some implementations, the method further comprises determining a pressure signal based on the transmitted optical signal. In certain implementations, the method further comprises determining the mechanical failure event based on the calculated SNR, the determined motor current, and the determined pressure signal.

In some implementations, the method further comprises determining a pressure signal based on the transmitted optical signal. In certain implementations, the method further comprises determining the mechanical failure event based on the calculated SNR, the determined motor current, and the determined pressure signal.

In some implementations, the time period is between about 1 to about 5 minutes. According to certain implementations, the time period is between about 5 to about 10 minutes.

According to a further implementation of the present disclosure, there is provided a method for operating a catheter-based blood pump system driven by a motor, the blood pump system comprising an inlet cannula and a pump having a rotor in a shroud. The method comprises actuating a rotor of the pump by sending electrical current to the rotor from the motor. The method further comprises detecting electrical current flowing to and from the motor. The method further comprises detecting a vibration of a component of the pump, or the cannula, motor or other system component. The method may further comprise adjusting the electrical current to the motor based on the detected vibration. In some implementations, the detected vibration is indicative of a bearing failure in the pump rotor or motor. In other implementations, detecting vibration includes detecting an optical signal from an optical sensor positioned on or near at least one of the shroud, the cannula, and the motor. In certain implementations, the method further comprises identifying a failure of the pump rotor by detecting a change in vibration of a system component (e.g., the pump or cannula) during a period when the electrical current to the motor is positive.

The systems and methods can apply to blood pump systems that have various pump configurations. For example, it can apply to pumps with onboard motors (e.g., the Impella systems) that have a motor coupled to the pump rotor and catheter, and to pumps that are external motors and a drive cable (e.g., the Hemopump style pump to convert torque supplied by the external motor).

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout, and in which.

DETAILED DESCRIPTION

To provide an overall understanding of the systems, method, and devices described herein, certain illustrative embodiments will be described. The systems, methods, and devices described herein provide for using an optical fiber sensor as a diagnostic tool to evaluate the performance and status of a catheter-based medical device. An evaluation device is used to calculate a signal to noise ratio (SNR) of an optical signal from the optical fiber sensor. The SNR can be used to determine the magnitude of the mechanical vibrations of the medical device, for example an intra cardiac blood pump. In instances of higher vibration, the SNR is much lower compared to instances of lower vibration. Additionally, while the medical device is running, a rise in the SNR signal coincides with the medical device experiencing a mechanical failure event. For example, an instantaneous spike on the SNR signal of a blood pump may coincide with a pump bearing failure. Conversely, in a static condition with no vibrations, no instantaneous shift is observed. There should be no hyperlinks in your application.

Using the SNR of the optical fiber sensor (either alone or in combination with other operational parameters) can facilitate earlier and more reliable detection of mechanical failure events and instability. Early and reliable detection of a mechanical failure in a blood pump can help prevent sudden and harmful stops of the pump and the associated adverse effects to the patients. The SNR of the optical fiber sensor can also help to determine device location within the body. Proper placement of the device within the body is important for optimal performance. Another advantage of using the SNR of the optical fiber sensor is that it can be used to detect vibration and assess device performance, stability, and temperature.

Figure 1:
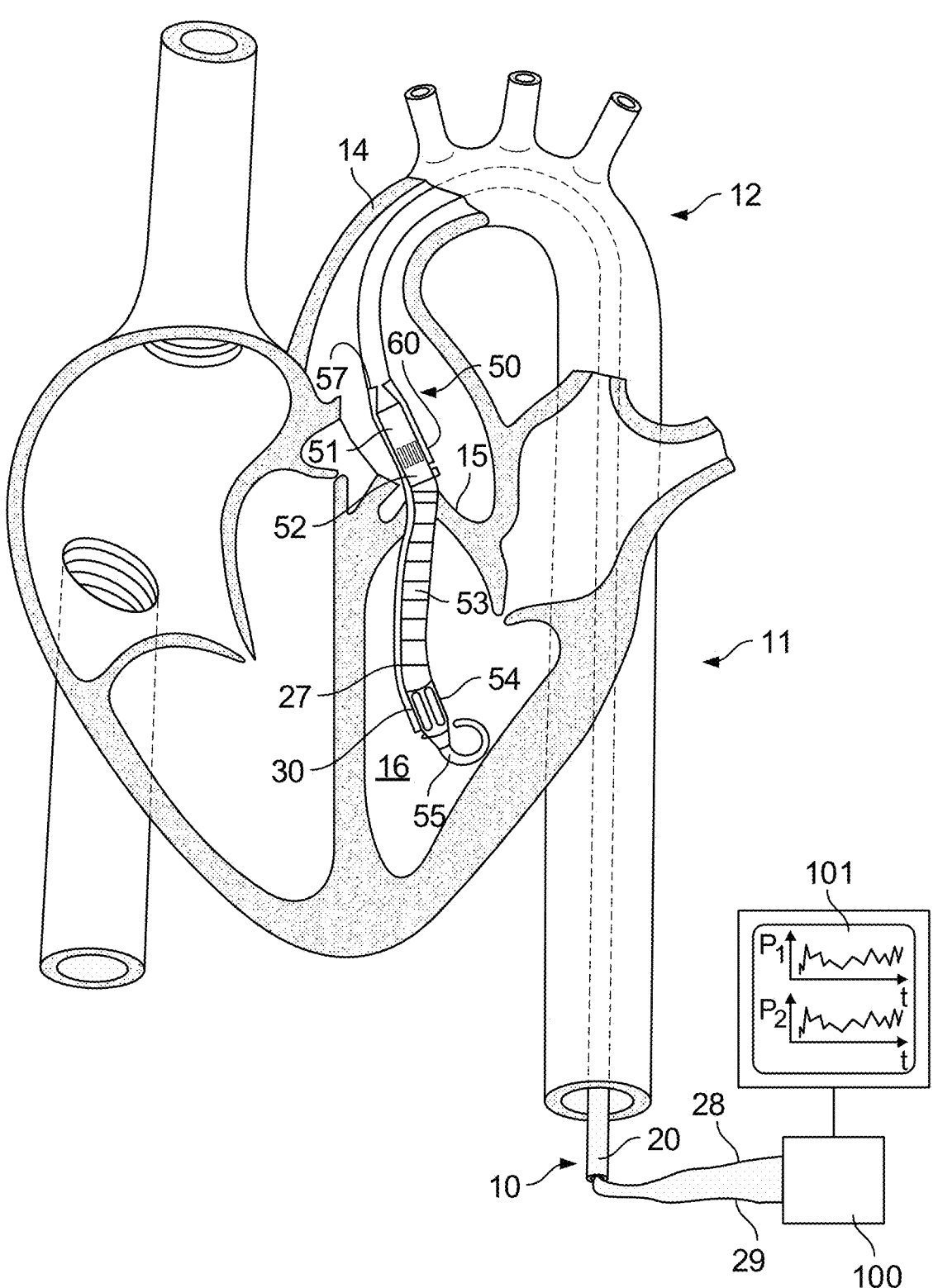
FIG. 1 shows an isometric view of an illustrative blood pump laid through the aorta, which extends through the aortic valve into the left ventricle and has one or more integrated optical fiber sensors.

FIG. 1 shows an intracardiac blood pump having a catheter 10 which is introduced into the descending aorta 11 retrograde. The descending aorta 11 is part of the aorta 12 which first ascends from the heart and then descends and has the aortic arch 14. At the beginning of the aorta 12 the aortic valve 15 connects the left ventricle 16 to the aorta 12, and the intracardiac blood pump extends through aortic valve 15. The blood pump comprises in addition to the catheter 10 a rotary pumping device 50 fastened at the distal end of the catheter hose 20. The pumping device 50 has a motor section 51 that couples to the catheter and a pump section 52 disposed distally from the motor section 51, as well as a flow cannula 53 protruding in the distal direction from the pump section 52. The pump section has a rotor within a shroud. The cannula has a distal inlet 54 and a proximal outlet, located proximal of the rotor. The motor speed of the rotary pumping device 50 depends on a motor current that drives the rotary pumping device 50. Distally of the suction inlet 54 there is provided a soft-flexible tip 55, configured for example as a "pigtail".

Various fluid, electrical and other lines extend through the catheter hose 20 for operating the pumping device 50. Of these, FIG. 1 shows a configuration having two optical fibers 28 and 29 which are attached at their proximal end to an evaluation device 100. These optical fibers 28 and 29 are respectively part of an optical pressure sensor whose sensor heads 60 and 30 are located outside of the housing of the pump section 52, on the one hand, and on the outside on the suction inlet 54, on the other hand. The sensor head 60 is in contact with blood flowing into the aorta and is thus able to detect optical signals within the blood flowing in the aorta (to measure aortic pressure and detect pump vibration). Sensor head 30 (when used) is positioned near the distal end of the pump within the left ventricle, so it contacts blood within the left ventricle to measure left ventricular pressure (and also detect pump or cannula vibration). Optical signal measurements are performed, for example, by transmitting a pulse (or continuous flow) of light into the blood stream and receiving a return pulse forming an optical sensor signal that can be returned to the evaluation device for processing. The return pulse is a reflection of the original pulse that is coupled back into the sensor head due to the deformation of the glass membrane of the sensor heads 30 and 60, as described further below. The optical signals from the sensor heads are transmitted to the evaluation device 100, which converts them into electrical signals and transmits and displays them on a display screen 101. Although two sensors are shown, the system may be configured for use with only one. As discussed further below, sensor head 60 is near the pump housing and motor section 51 where vibrations would be the largest, so sensor head 60 may be better suited than sensor 30 to detect a mechanical failure event. But sensor 30 can also be used to detect changes in the cadence of cannula motion during pump that may also be indicative of pump failure. The motor current of the rotary pumping device 50 is also transmitted to the evaluation device 100 through electrical leads within the catheter and can be displayed on display screen 101.

The sensors can provide various beneficial information. With a sensor head 60 (and optionally another sensor, such as sensor 30) positioned inside the patient, the system can measure the aortic pressure. If other sensors are used, other pressures may also be detected, such as the ventricular pressure by the sensor head 30. The pressure measurements can also provide contractility measurements for tracking the recovery of the heart. Contractility represents the inherent ability of the heart muscle to contract. The pressure signals also can be evaluated to identify a pressure difference which can be used for computing the flow of blood through the cannula of the pumping device 50. The ventricular pressure and the volume of blood flow during a heartbeat can be used to determine contractility. The distal sensor head 30 can also extend into the soft-flexible tip 55, being positioned, for example, so the head protrudes from the tip, for detecting ventricular pressure. By detecting ventricular pressure with sensor head 30 the clinician can detect when the pump has crossed the aortic valve. Moreover, the sensor is sensitive enough to detect slight bending of the tip 55 which can guide the clinician to more efficiently push the pump across the valve. When the pump is located near the cardiac wall, as in FIG. 1, the sensor can also detect excessive pressure on the cardiac wall as a result of bending or kinking, as for example, caused by the inlet sucking the mitral valve and chordae inside the ventricle. Detection of this state allows the user to rotate or withdraw the pump.

Figure 2:
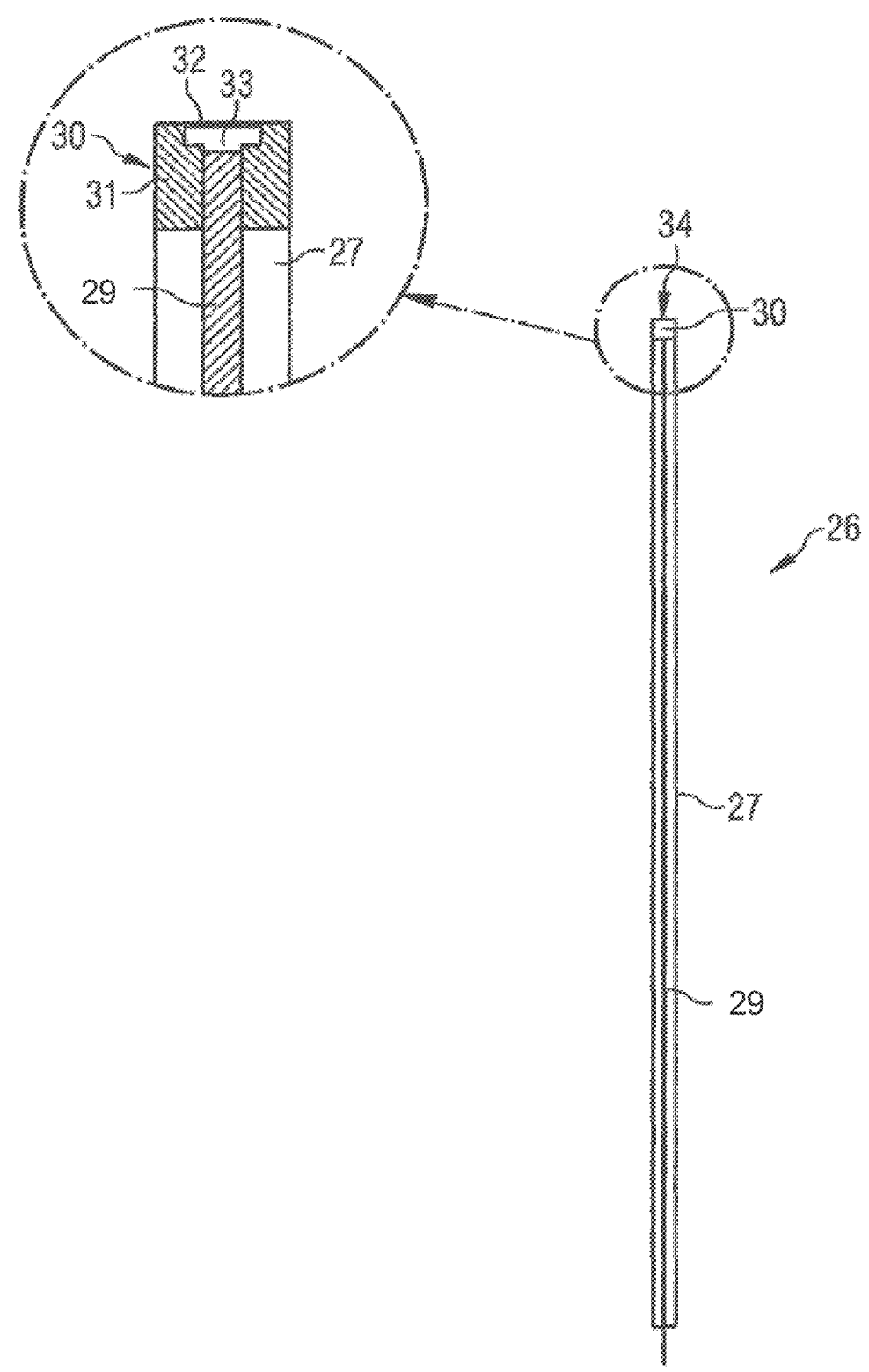
FIG. 2 shows a cross-sectional view of the optical fiber sensor of FIG. 1 having an optical fiber.

Electro-optical pressure measurement is further illustrated in FIG. 2. FIG. 2 shows a pressure-measuring catheter 26 having a lumen 27 in which an optical fiber 29 (and optionally 28) is freely movable. The catheter 26 can preferably be made of nitinol or another shape-memory alloy or a polymer hose. As shown in FIG. 1, the catheter 26 exits from the catheter hose 20 at an exit point 57 and is guided along the flexible flow cannula 53 (e.g., on the outside). At the distal end 34 of the optical fiber 29 (or 28) the pressure-measuring catheter has a sensor head (such as 30 or 60) having a head housing 31 which contains a thin glass membrane 32 abutting a cavity 33. The light impacts the glass membrane 32 and passes into and out of the fiber 28 (or 29) in a low-loss manner (i.e., low attenuation loss over the length of the fiber). The glass membrane 32 is pressure-sensitive and is deformed according to the magnitude of the pressure acting on the sensor head 30 (or 60). The deformation of the glass membrane 32 causes the light to be reflected and coupled back into the optical fiber 28 (or 29). At the proximal end of the optical fiber 28 (or 29), i.e. in the evaluation device 100, a digital camera, e.g. a CCD camera or a CMOS, receives the incoming light and generates a pressure-dependent electrical signal. For example, the camera may receive the incoming light and generate an optical image or optical pattern and transmit that image or pattern to a signal processor in the evaluation device, which is configured to receive the image or pattern as an input and use it to compute a pressure signal. In some embodiments, the signal processor is configured to use the computed pressure signal to control the power supply to the motor-operated pumping device 50. For example, if the computed pressure signal is low, the signal processor increases the power supply to the motor-operated pumping device 50. If the computed pressure signal is high, the signal processor decreases the power supply to the motor-operated pumping device 50.

As noted above, the distal sensor head 30 extends into the soft-flexible tip 55, for detecting the ventricular pressure at the tip 55 of the pump. As shown, the head 60 is positioned proximal of the pump and remains in the aorta, for detecting aortic pressure. Its signal is detected and transmitted to the evaluation device 100. The signals from heads 30 and 60 can be compared at the evaluation device 100 and used to compute a differential pressure signal/measurement, which is used for pump placement and monitoring. The differential signal or measurement can also be used in combination with motor current and other parameters for monitoring pump placement and performance, as discussed herein. Moreover, this enables the bending of the tip 55 to be detected very sensitively, which makes a simpler valve crossing possible. When the pump is located near the wall, as in FIG. 1, an excessive pressure on the cardiac wall as a result of the bending or kinking can moreover be detected. The latter can also lead to the inlet sucking on cardiac structures. Detection of this state can be revised by the user by rotating or withdrawing the pump.

The distal sensor head 60 and optical fiber 28B can be used to detect a mechanical failure event at the motor section

51 of the rotary pumping device 50. The optical signal that is transmitted from the distal sensor head 60 to the evaluation device 100 using optical fiber 28B can be used by the evaluation device 100 to calculate the SNR of the optical signal. The SNR is correlated to the mechanical vibrations of the rotary pumping device 50. When the rotary pumping device 50 is stopped, the mechanical vibrations of the rotary pumping device 50 are at a minimum. During this state, the SNR is relatively large because the noise level of the optical signal is low. When the rotary pumping device 50 is running, the mechanical vibration of the rotary pumping device 50 increases. During normal operation, the SNR is relatively low because the noise level of the optical signal is large, and the motor current is greater than zero (because the motor is driving current to the pump). The SNR when the rotary pumping device 50 is running in that normal condition can be considered a baseline SNR, and can be used to determine a threshold SNR for detecting changes in the SNR that may signal a mechanical failure event. During a mechanical failure event, the SNR may increase over a short period of time when the speed of the rotary pumping device 50 decreases, for example due to a bearing failure or partial jamming of the rotor, but the motor current is positive indicating that the motor is still working.

Increases in SNR above the baseline (or other threshold) can be detected and assessed for evaluating pump performance. In some applications, the evaluation device 100 determines whether a mechanical failure event has occurred by determining whether an increase in the SNR in a time period exceeds the threshold during a period of time (or at a point in time) when the pump is operating (indicated for example by the motor current being positive). The evaluation device 100 would be configured with the threshold based on the baseline SNR prior to the mechanical failure event. For example, the threshold can be set as a factor (e.g., one-quarter, one-third, one-half, or double) of a magnitude of the baseline SNR. Other threshold values can be used by the evaluation device 100 to determine a mechanical failure event. Alternatively, the evaluation device 100 can receive an input from a user indicating the threshold for assessing changes in the SNR. The time period during which the SNR is evaluated can be any period of time desired. For example, the input time period can be one minute, between about one to about five minutes, between about five to about ten minutes, or between about ten minutes to about 20 minutes. Other time periods can be used by the evaluation device 100 to determine a mechanical failure event. If the evaluation device 100 determines that a mechanical failure event has occurred, e.g., if the SNR exceeds the threshold during the evaluation time period while the motor current remains positive, the evaluation device 100 can generate and output an indicator associated with the mechanical failure event. The indicator can be displayed on display screen 101.

Figures 3, 4:
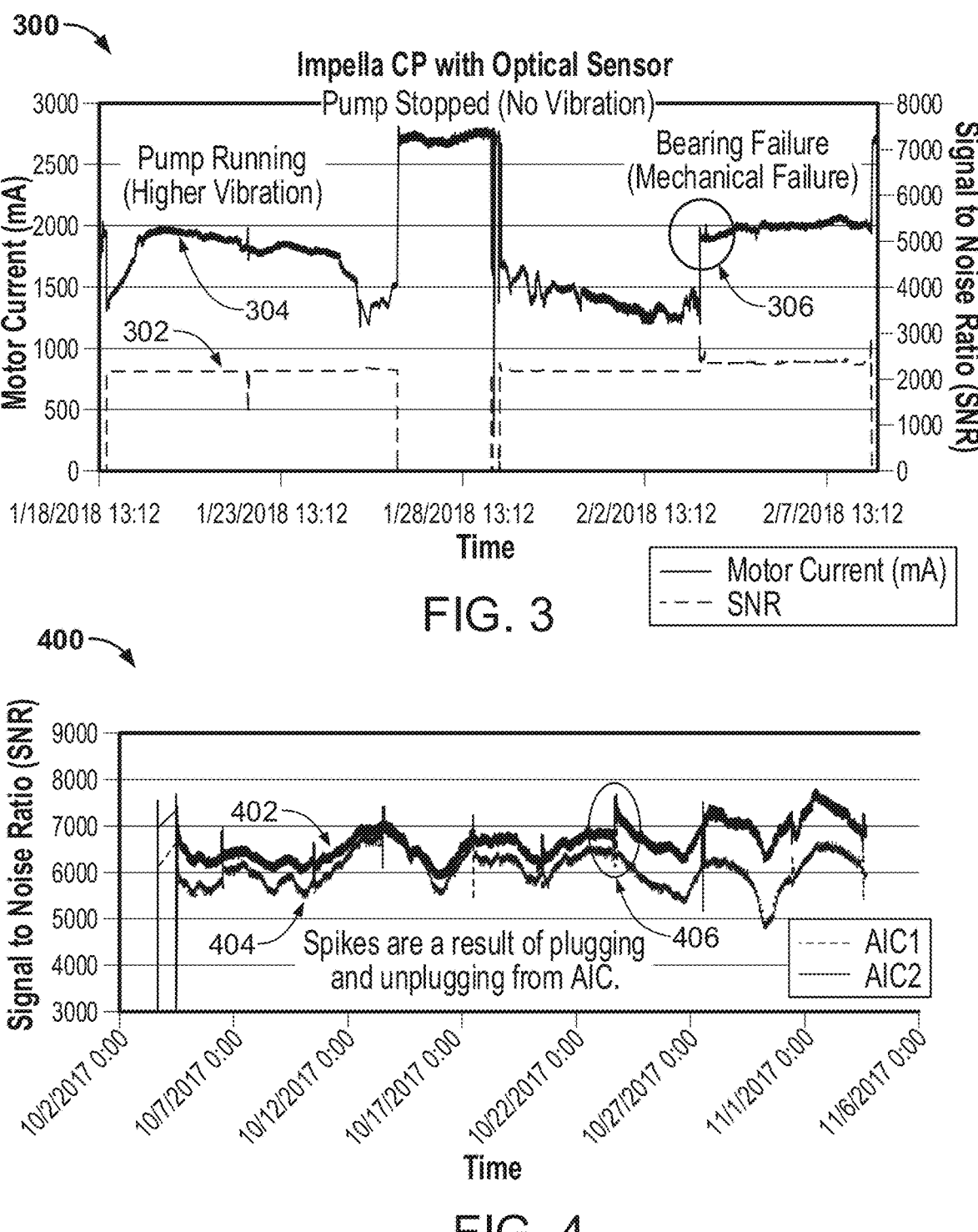
FIG. 3 shows an illustrative graph of continuous logging of the motor current of the blood pump of FIG. 1 and a calculated signal to noise ratio based on a signal from an optical fiber sensor of FIGS. 1 and 2.
FIG. 4 shows an illustrative graph of continuous logging of a calculated SNR based on a signal from the optical fiber sensor of FIG. 2.

FIG. 3 shows an illustrative graph 300 of continuous logging of the motor current of the rotary pumping device 50 of FIG. 1 and a calculated SNR based on a signal from an optical fiber sensor of FIGS. 1 and 2 over a period of days. Graph 300 includes motor current 302 and SNR 304. The motor current 302 of the rotary pumping device 50 is transmitted to the evaluation device 100 over a period of days and is greater than zero when the rotary pumping device 50 is running, and is zero when the motor is stopped. The baseline SNR would be the SNR when the rotary pumping device 50 is running because the SNR is relatively low. During a bearing failure event 306, the SNR 304 increases over a short time period (e.g., minutes in the example of FIG. 3) from the baseline SNR. For example, as shown in FIG. 3, the SNR 304 increases from the baseline SNR of approximately 3500 to an SNR 304 of 5500. The SNR increases over this short period of time because the speed of the rotary pumping device 50 has decreased due to a bearing failure, and accordingly the vibrations of the pump would slow. In this example, the increase in SNR over the short time period is approximately 2000. The evaluation device 100 determines a threshold SNR for detecting a bearing failure event 306. For example, the evaluation device 100 can determine the threshold based on the baseline SNR because the baseline SNR is the SNR during normal operation of the pump. A large deviation from the SNR during pump operation indicates the bearing failure event; it could also indicate other failures of the pump. The evaluation device 100 can determine that the threshold is a fixed and/or predetermined amount of the baseline SNR. For example, as shown in FIG. 3, the evaluation device 100 can determine that the threshold is one-half of the baseline SNR (3500), or 1750. The evaluation device 100 determines that a bearing failure event 306 occurred because the motor current is greater than zero (the rotary pumping device 50 is running) and the increase in the SNR over the short time period (2000) is greater than the threshold (1750). At least one advantage of using the SNR 304 of the optical fiber sensor in combination with the motor current 302 is that it allows for earlier and more reliable detection of the pump failure event 306 (for example the bearing failure, which is otherwise hard to detect). Unlike previous generations of blood pumps, the systems and methods of this disclosure contemplate using optical sensors to assess pump performance by detecting signals from the optical fiber sensor such as SNR 304. The sensors may also be used to monitor the placement of the pump in the vasculature.

FIG. 4 shows an illustrative graph 400 of continuous logging of calculated SNRs based on a signal from an optical fiber sensor of FIG. 2 over a period of over a month. Graph 400 includes first SNR 402 and second SNR 404. First SNR 402 and second SNR 404 are each obtained from evaluation device 100 at different points in time and compared in graph 400. During normal operation over a period of days, first SNR 402 and second SNR 404 do not increase over a short period of time. In order to simulate bearing failure events 406, the power delivered to the blood pumps was turned off During a bearing failure event 406, first SNR 402 and second SNR 404 increase over a short period of time due to losses of power. The losses of power decrease the speed of the rotary pumping device 50 such that it results in a decrease in vibrations. The decrease in vibrations simulates a bearing failure event 406. As described in relation to FIG. 3, the evaluation device 100 can determine that a bearing failure event 406 occurred based on the first SNR 402 and the second SNR 404. FIG. 4 illustrates the reliability of using SNR signals as an indicator of bearing failure because there are few, if any, false positives.

Figure 5A:
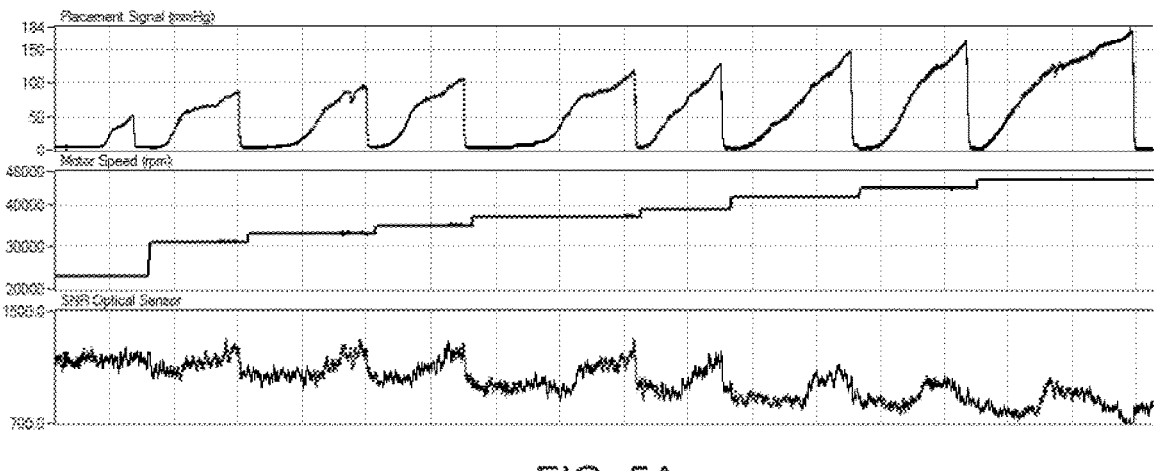
FIGS. 5A-C shows an illustrative graph of continuous logging of the placement signal and motor current of the blood pump of FIG. 1, and a calculated SNR based on a signal from the optical fiber sensor of FIGS. 1 and 2.
Figure 5B:
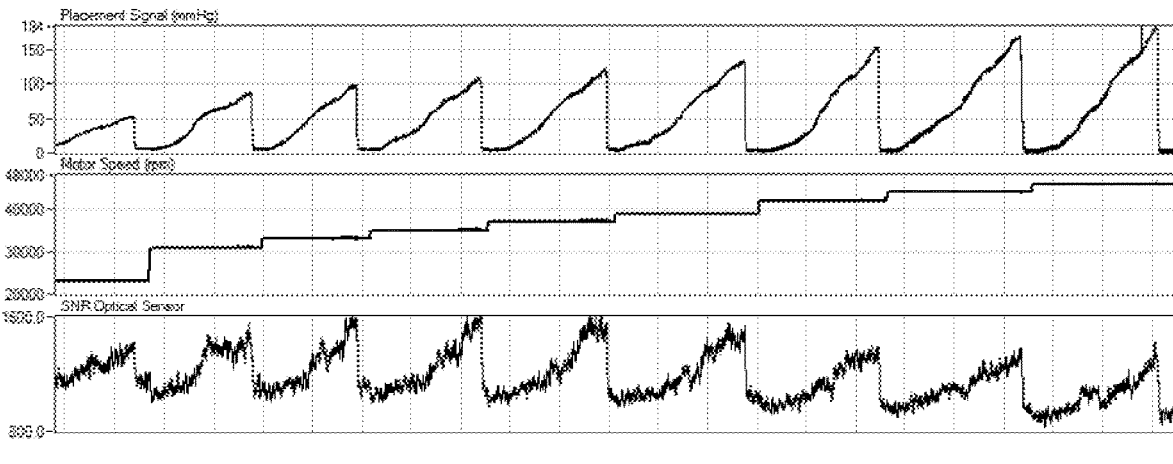
Figure 5C:
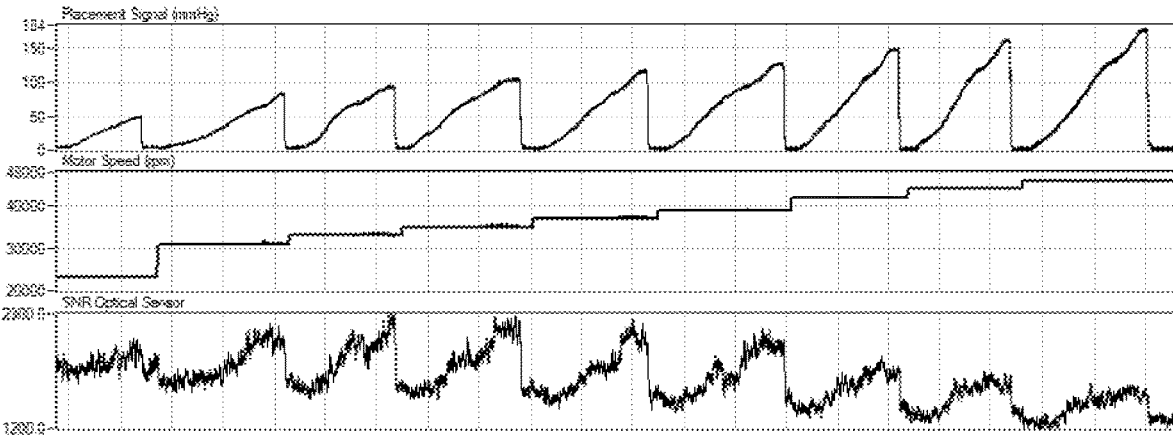

Alternatively, the evaluation device 100 can use the placement signal, the motor current, and the SNR to determine whether a mechanical failure event has occurred. The placement signal is calculated by the evaluation device 100 from the transmitted optical signal of sensor head 60 and indicates a pressure. The placement signal can be used in combination with the process described above in relation to FIGS. 3 and 4 to determine mechanical failure events. For example, FIGS. 5A-C shows three illustrative graphs of continuous logging of the placement signal and motor current of the rotary pumping device 50 of FIG. 1, and a calculated SNR based on a signal from the optical fiber sensor of FIGS. 1 and 2. As shown in each of the three graphs of FIG. 5A-C, when the placement signal is stable, the evaluation device can determine a decrease in SNR as the motor speed is increased, because the mechanical vibrations of the rotary pumping device 50 increase with increasing motor speed. The evaluation device 100 would identify a mechanical failure event if the placement signal is stable, the motor speed/current is stable, and the SNR increases over a short period of time. For example, the SNR increase can be instantaneous. In some examples, the SNR increase can occur over a time period between about 100 milliseconds to about 1 second or between about 1 second to about 10 seconds. In other examples, the SNR increase can occur over a time period between about one to about five minutes or between about five to about ten minutes. Using SNR in combination with the placement signal and motor current is advantageous because the placement signal provides more information with respect to the location of the pump in the body of the patient.

Figure 6:
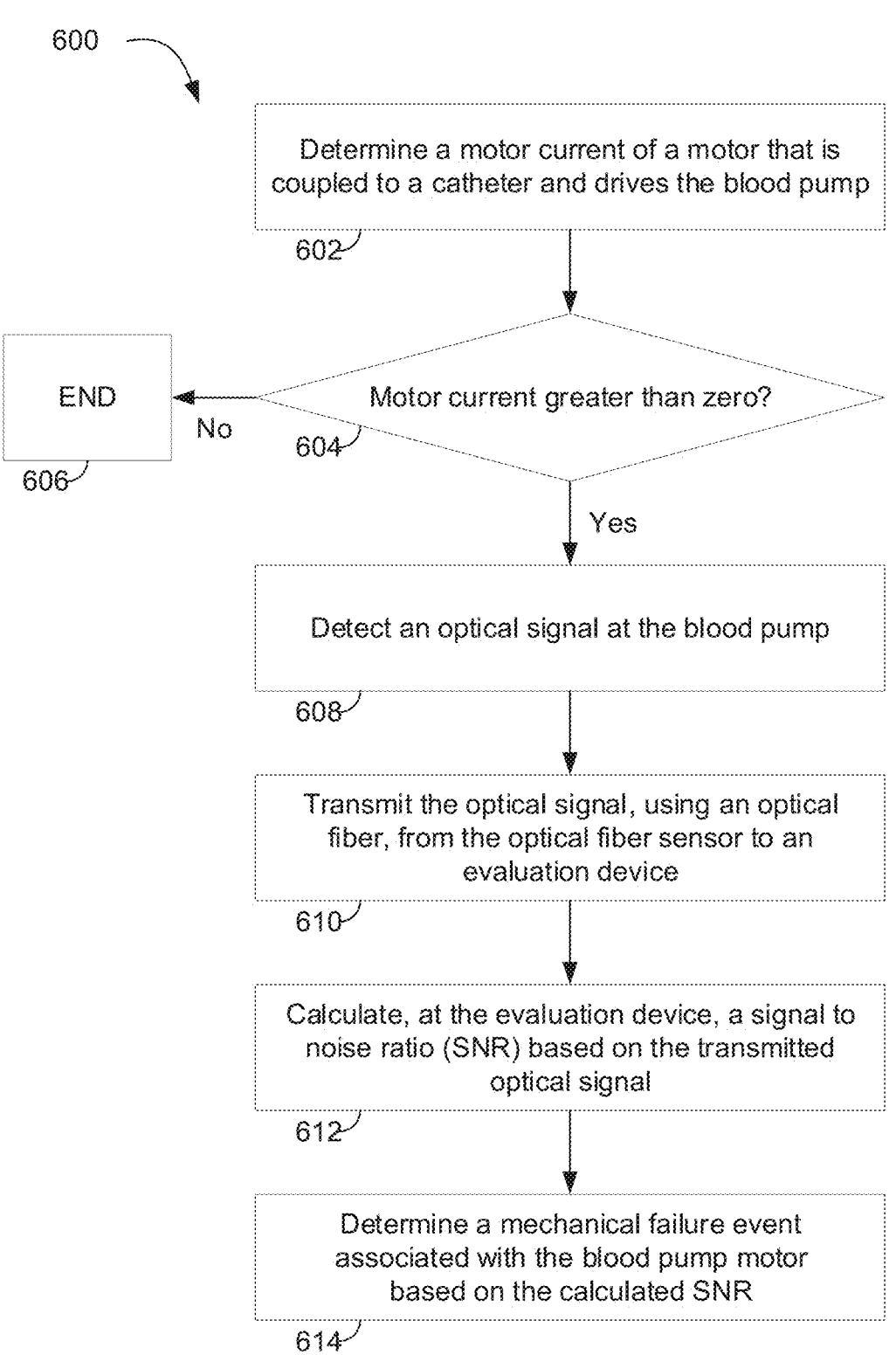
FIG. 6 shows an illustrative method for determining a mechanical failure event associated with the blood pump of FIG. 1.

FIG. 6 shows a process 600 of determining a mechanical failure event associated with the blood pump 50 of FIG. 1. At step 602, the evaluation device 100 determines a motor current of a motor that drives a blood pump. For example, as mentioned above in relation to FIGS. 1 and 2, the motor current of the rotary pumping device 50 is transmitted to the evaluation device 100 and can be displayed on display screen 101.

At step 604, the evaluation device 100 determines whether the motor current is greater than zero. For example, the motor current is zero if the rotary pumping device 50 is stopped, and the motor current is greater than zero if the rotary pumping device 50 is running. If the motor current is zero, process 600 ends at step 606. However, if the motor current is greater than zero, process 600 proceeds to step 608.

At step 608, the evaluation device 100 detects an optical signal at the blood pump. For example, as mentioned above in relation to FIGS. 1 and 2, the glass membrane 32 is pressure-sensitive and is deformed in response to the amount of pressure acting on the sensor head 60 (or 30). For example, the deformation of the glass membrane 32 causes the light to be reflected and coupled back into the optical fiber 28 (or 29).

At step 610, optical fiber 28 transmits the optical signal from the optical fiber sensor to an evaluation device. For example, as mentioned above in relation to FIGS. 1 and 2, the optical signals transmitted by the sensor heads 30 and 60 can be converted into electrical signals in the evaluation device 100 and displayed e.g. on a display screen 101.

At step 612, the evaluation device 100 calculates an SNR based on the transmitted optical signal. For example, the optical signal that is transmitted from the distal sensor head 60 to the evaluation device 100 using optical fiber 28 can be used by the evaluation device 100 to calculate the SNR of the optical signal. The SNR is linked to the mechanical vibrations of the rotary pumping device 50. When the rotary pumping device 50 is stopped, the motor current is zero and the mechanical vibrations of the rotary pumping device 50 are at a minimum. During this state, the SNR is relatively large because the noise level of the optical signal is low. When the rotary pumping device 50 is running, the motor current is greater than zero and the mechanical vibration of the rotary pumping device 50 increases. During this state, the SNR is relatively low because the noise level of the optical signal is large.

At step 614, the evaluation device 100 determines a mechanical failure event associated with the blood pump motor based on the calculated SNR. As mentioned above in relation to FIGS. 1 and 2, when the rotary pumping device 50 is stopped, the mechanical vibrations of the rotary pumping device 50 are at a minimum. During this state, the SNR is relatively large because the noise level of the optical signal is low. When the rotary pumping device 50 is running, the motor current is greater than zero and the mechanical vibrations of the rotary pumping device 50 increase. A rapid rise in SNR from the baseline (e.g., when the pump is operating normally) signals a mechanical problem with the pump. For example, during a failure state, the SNR is relatively low because the noise level of the optical signal is large but the motor current is greater than zero indicating that the motor is driving the pump with current but the pump is not pumping (or is slowing). The evaluation device 100 determines a threshold SNR for detecting a mechanical failure event. In one aspect, the evaluation device can receive the threshold SNR from a user input. Alternatively, the SNR when the rotary pumping device 50 is running can be considered a baseline SNR, and can be used to determine the threshold SNR for detecting a mechanical failure event. During a mechanical failure event, the SNR increases over a short period of time because the speed of the rotary pumping device 50 has decreased, for example, due to a bearing failure. Step 614 is described in greater detail below, in relation to process 700 of FIG. 7.

Figure 7:
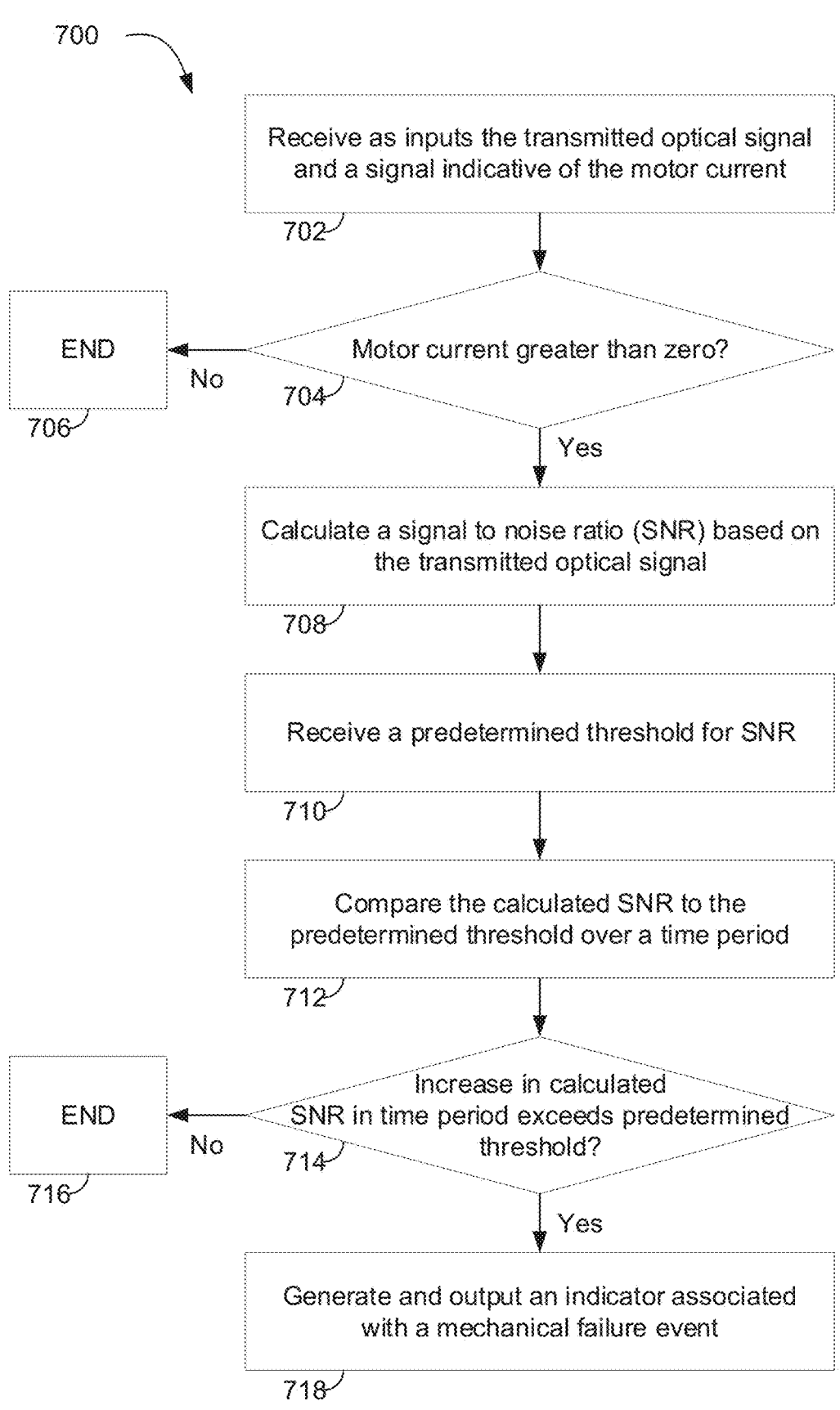
FIG. 7 shows an illustrative method for generating and outputting an indicator associated with the determined mechanical failure event of FIG. 6 and the blood pump of FIG. 1.

FIG. 7 shows a process 700 of generating and outputting an indicator associated with the determined mechanical failure event of process 600 and the blood pump of FIG. 1. At step 702, the evaluation device 100 receives as inputs the transmitted optical signal and a signal indicative of the motor current. For example, as mentioned above in relation to FIGS. 1 and 2, the motor current of the rotary pumping device 50 is transmitted to the evaluation device 100 and can be displayed on display screen 101 and the optical signals transmitted by one or both of the sensor heads 30 and 60 can be converted into electrical signals in the evaluation device 100 and displayed e.g. on a display screen 101.

FIG. 7 shows a process 700 of generating and outputting an indicator associated with the determined mechanical failure event of process 600 and the blood pump of FIG. 1. At step 702, the evaluation device 100 receives as inputs the transmitted optical signal and a signal indicative of the motor current. For example, as mentioned above in relation to FIGS. 1 and 2, the motor current of the rotary pumping device 50 is transmitted to the evaluation device 100 and can be displayed on display screen 101 and the optical signals transmitted by one or both of the sensor heads 30 and 60 can be converted into electrical signals in the evaluation device 100 and displayed e.g. on a display screen 101.

But during pump failure or malfunctioning, the SNR changes, which the following steps help identify. At step 708, the evaluation device 100 calculates an SNR based on the transmitted optical signal. For example, the optical signal that is transmitted from the proximal sensor head 60 to the evaluation device 100 using optical fiber 28 can be used by the evaluation device 100 to calculate the SNR of the optical signal. The SNR is correlated to the mechanical vibrations of the rotary pumping device 50.

At step 710, the evaluation device 100 receives a predetermined threshold for the SNR. For example, the SNR when the rotary pumping device 50 is running can be considered a baseline SNR, and can be used to determine a threshold SNR for detecting a mechanical failure event. The evaluation device 100 can determine the threshold based on the baseline SNR prior to the mechanical failure event. For example, the threshold can be a factor (e.g., one-quarter, one-half, or double) of a magnitude of the baseline SNR.

At steps 712 and 714, the evaluation device 100 compares the calculated SNR to the predetermined threshold over a time period and determines whether an increase in the calculated SNR in the time period exceeds the predetermined threshold. For example, during a mechanical failure event, the SNR increases over a short period of time because the speed of the rotary pumping device 50 has decreased due to a failure of a pump component (such as a bearing failure). The evaluation device 100 can determine whether a mechanical failure event has occurred by determining whether an increase in the SNR in a time period exceeds the threshold. The time period can be any period of time established by a user. For example, the period of time can be greater than one minute. In other examples, the time period can be between about one to about five minutes or between about five to about ten minutes. As illustrated in relation to FIG. 3, the evaluation device 100 can determine that a failure event 306 occurred because the motor current is greater than zero (the rotary pumping device 50 is running) and the increase in the SNR over the short time period (2000) is greater than the threshold (1750).

If the evaluation device 100 determines that the increase in the calculated SNR in the time period does not exceed the predetermined threshold, process 700 ends at step 716. However, if the evaluation device 100 determines that the increase in the calculated SNR in the time period does exceed the predetermined threshold, process 700 continues to step 718.

At step 718, the evaluation device 100 generates and outputs an indicator associated with a mechanical failure event. For example, if the evaluation device 100 determines that a mechanical failure event has occurred, the evaluation device 100 can generate and output an indicator associated with the mechanical failure event. The indicator can be displayed on display screen 101. The device 100 can also send a control signal to shut off the motor, in response to the determination.

Figure 8:
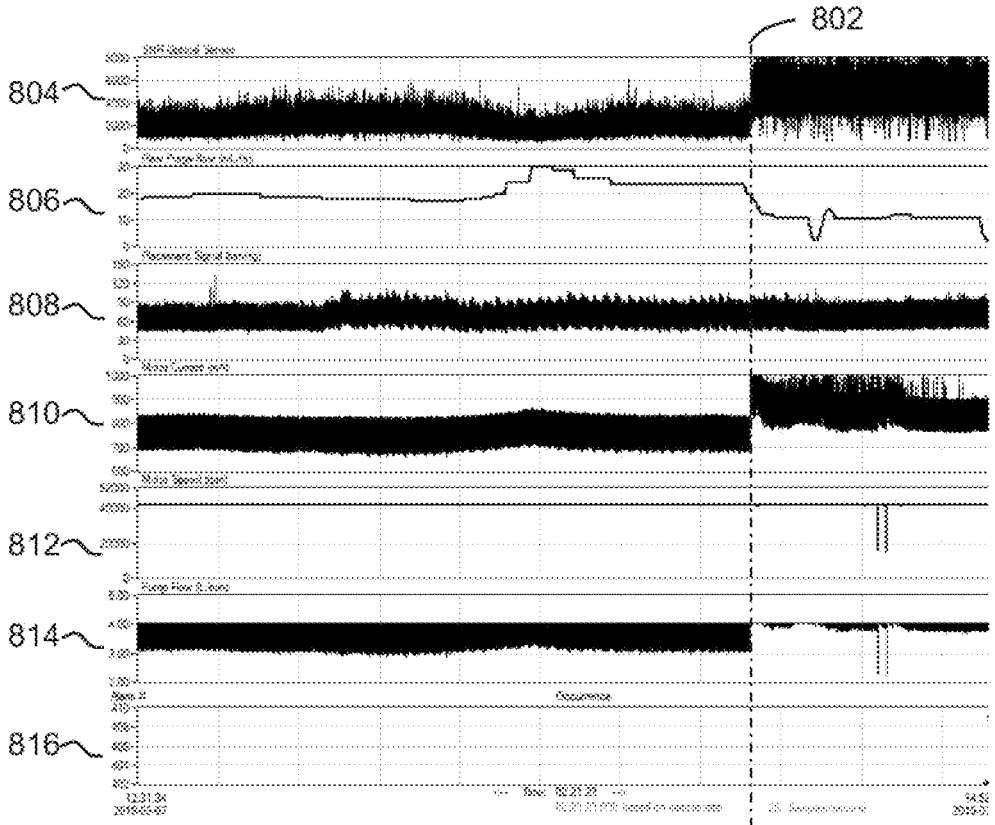
FIG. 8 shows seven illustrative graphs representing data collected from a blood pump system.
Figure 9:
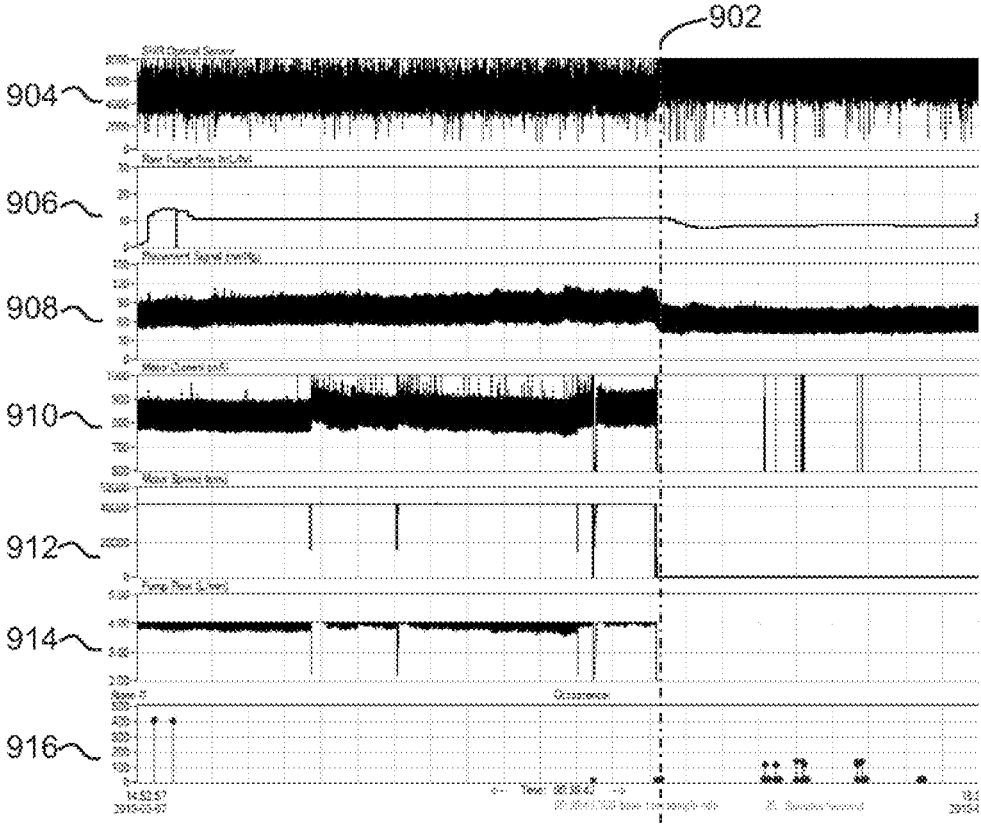
FIG. 9 shows seven illustrative graphs representing data collected from a blood pump system during a period of time after that shown in FIG. 8.

FIGS. 8-9 show data collected from a blood pump system with a mechanical failure. FIG. 8 shows seven illustrative graphs representing data collected from the blood pump system. Graph 804 shows SNR (unitless) of an optical sensor, graph 806 shows raw purge flow (mL/hr), graph 808 shows placement signal (mmHg), graph 810 shows motor current (mA), graph 812 shows motor speed (rpm), graph 814 shows pump flow (L/min), and graph 816 shows alarm occurrence (alarm number). Graphs 804 through 816 are shown in the same time scale and beginning at the same time (12:31:34 on Mar. 7, 2019). At time 802, the SNR (shown in graph 804) increased significantly relative to the SNR prior to time 802. Prior to time 802, the average SNR was around 2500 with maximum values around 6000 and minimum values around 1000. After time 802, the average SNR was around 5000, with maximum values over 8000 and minimum values around 1000. At time 802, the motor current (shown in graph 810) also increased rapidly over a short period of time, jumping from an average value of around 760 mA with maximum values around 830 mA and minimum values around 690 mA prior to time 802, to an average value of around 850 mA with maximum values over 1000 mA and minimum values around 780 mA after time 802. The amplitude of the pump flow variance (shown in graph 814) decreased at time 802 as well, from an average amplitude of around 1 L prior to time 802 to an average amplitude of around 0.2 L after time 802. These increases in SNR and motor current at time 802 indicate a mechanical problem or instability in the blood pump system—a problem corresponding in time to a bearing failure that later led to a motor failure as shown in FIG. 9 and described below.

FIG. 9 is a continuation of the graphs shown in FIG. 8 (beginning at 14:52:57 on Mar. 7, 2019, where the x-axis of the graphs shown in FIG. 8 ended). Graph 904 shows a continuation of the SNR of graph 804, graph 906 shows a continuation of the raw purge flow signal of graph 806, graph 908 shows a continuation of the placement signal of graph 808, graph 910 shows a continuation of the motor current signal of graph 810, graph 912 shows a continuation of the motor speed signal of graph 812, graph 914 shows a continuation of the pump flow signal of graph 814, and graph 916 shows a continuation of the alarm occurrence signal of graph 816. At time 902, the motor in the blood pump system failed. As can be seen in FIG. 9, when the motor failed (after the bearing failure at time 802), the SNR increased, the placement signal decreased, the motor current decreased to approximately zero mA, the motor stopped running (the motor speed became zero rpm), the pump flow stopped, and an alarm (shown in graph 916) was triggered. The increases in SNR and motor current at time 802 were indicative of mechanical problems in the blood pump system approximately one hour prior to the motor failure at time 902. At least one benefit of identifying increases in SNR and motor current (e.g., at time 802) is earlier and more reliable detection of mechanical problems and instability in the blood pump system. In some implementations, such an increase in SNR, motor current, or both may trigger an alarm, a motor shutdown, or prompt a user to remove (and, in some cases, replace) the blood pump system before the motor fails.

In view of the foregoing, the person of ordinary skill will appreciate that the present disclosure provides for using an optical fiber sensor as a diagnostic tool to evaluate the performance and status of a catheter-based medical device. Although the embodiments and features described herein are specifically described for use in connection with a percutaneous heart pump system, it will be understood that the components and other features outlined below may be combined with one another in any suitable manner and may be adapted and applied to other types of medical devices such as electrophysiology study and catheter ablation devices, angioplasty and stenting devices, angiographic catheters, peripherally inserted central catheters, central venous catheters, midline catheters, peripheral catheters, inferior vena cava filters, abdominal aortic aneurysm therapy devices, thrombectomy devices, TA VR delivery systems, cardiac therapy and cardiac assist devices, including balloon pumps, cardiac assist devices implanted using a surgical incision, and any other venous or arterial based endoluminal introduced catheters and devices.

The foregoing is merely illustrative of the principles of the disclosure, and the systems, methods, and devices can be practiced by other than the described embodiments, which are presented for purposes of illustration and not of limitation. It is to be understood that the systems, methods, and devices disclosed herein, while shown for use in a system percutaneous heart pumps, may be applied to systems, methods, and devices for other implantable heart pumps or implantable cardiac assist devices.

Variations and modifications will occur to those of skill in the art after reviewing the present disclosure. The various features described or illustrated above, including any components thereof, may be combined or integrated in other systems. Moreover, certain features may be omitted or not implemented. The various implementations described or illustrated above may be combined in any manner.

Examples of changes, substitutions, and alterations are ascertainable by one skilled in the art and could be made without departing from the scope of the information disclosed herein. All references cited herein are incorporated by reference in their entirety and made part of this application.

The invention claimed is:

1. A method for operating a catheter-based blood pump system driven by a motor, the blood pump system comprising an inlet cannula and a pump having a rotor in a shroud, comprising the steps of:

actuating the rotor of the pump by sending electrical current to the rotor from the motor, detecting electrical current flowing to and from the motor, detecting a vibration of a component of the pump by measuring an optical signal from an optical sensor positioned on a location of the component that contacts blood flowing from the pump, and adjusting the electrical current to the motor based on the detected vibration.

2. The method of claim 1, wherein the detected vibration is indicative of a bearing failure in the pump.

3. The method of claim 1, wherein the optical sensor is positioned on or near at least one of the shroud, the cannula, and the motor.

4. The method of claim 1, further comprising identifying a failure of the rotor by detecting a change in the vibration of the pump or cannula during a period when the electrical current to the motor is positive.

* * * * *